(12) United States Patent
Simon

(10) Patent No.: US 8,486,692 B2
(45) Date of Patent: Jul. 16, 2013

(54) CELL CULTURE APPARATUS AND ASSOCIATED METHODS

(75) Inventor: Eric M. Simon, Salt Lake City, UT (US)

(73) Assignee: Acme Biosystems LLC, Salt Lake City, UT (US)

( * ) Notice: Subject to any disclaimer, the term of this patent is extended or adjusted under 35 U.S.C. 154(b) by 332 days.

(21) Appl. No.: 12/514,798

(22) PCT Filed: Nov. 14, 2007

(86) PCT No.: PCT/US2007/023783
§ 371 (c)(1),
(2), (4) Date: May 13, 2009

(87) PCT Pub. No.: WO2008/060521
PCT Pub. Date: May 22, 2008

(65) Prior Publication Data
US 2010/0055790 A1    Mar. 4, 2010

Related U.S. Application Data

(60) Provisional application No. 60/865,797, filed on Nov. 14, 2006.

(51) Int. Cl.
| C12M 1/24 | (2006.01) |
| C12M 1/18 | (2006.01) |
| C12N 5/02 | (2006.01) |
| B01L 3/00 | (2006.01) |
| B28B 23/00 | (2006.01) |

(52) U.S. Cl.
USPC ............... 435/297.5; 435/305.1; 435/305.2; 435/383; 435/304.1; 264/250; 264/251; 422/551; 422/552; 422/553

(58) Field of Classification Search
USPC ............ 435/383, 297.5, 304.1, 297.1, 305.2, 435/305.1; 422/102, 551, 552, 553; 264/251, 264/250
See application file for complete search history.

(56) References Cited

U.S. PATENT DOCUMENTS

| 5,319,436 | A | * | 6/1994 | Manns et al. ................. 356/246 |
| 6,340,589 | B1 | | 1/2002 | Turner et al. |
| 6,528,302 | B2 | | 3/2003 | Turner et al. |
| 6,943,009 | B2 | | 9/2005 | Lacey et al. |
| 7,347,977 | B2 | | 3/2008 | Guelzow et al. |
| 7,767,153 | B2 | | 8/2010 | Guelzow et al. |
| 2001/0051112 | A1 | * | 12/2001 | Gulzow et al. ................ 422/102 |
| 2003/0215940 | A1 | * | 11/2003 | Lacey et al. ............... 435/305.2 |
| 2004/0023374 | A1 | | 2/2004 | Rappaport et al. |
| 2004/0063199 | A1 | * | 4/2004 | Takayama et al. ......... 435/287.2 |
| 2005/0106717 | A1 | * | 5/2005 | Wilson et al. .............. 435/297.5 |
| 2007/0254356 | A1 | | 11/2007 | Wilson et al. |
| 2008/0084004 | A1 | | 4/2008 | Guelzow et al. |

\* cited by examiner

*Primary Examiner* — William H Beisner
*Assistant Examiner* — Danielle Henkel

(57) ABSTRACT

A cell culture apparatus consists of a vessel or array of vessels, each comprising a substantially flat bottom and substantially vertical sides, and composed of a substantially gas permeable material. The inner bottom surface of the vessel is commonly textured to provide the cells with adequate features for attachment and spreading. The vessel may include an integral annular flange which can be used to suspend the vessel from a suspensory element of a rack structure. To promote cell attachment and growth, the inner surfaces of the vessel bottom and sides may be coated with commonly available bio-active materials. Cells cultured in the system commonly grow in three dimensions for extended periods of time, and often produce significantly higher quantities of cellular products than cells grown in conventional labware.

23 Claims, 14 Drawing Sheets

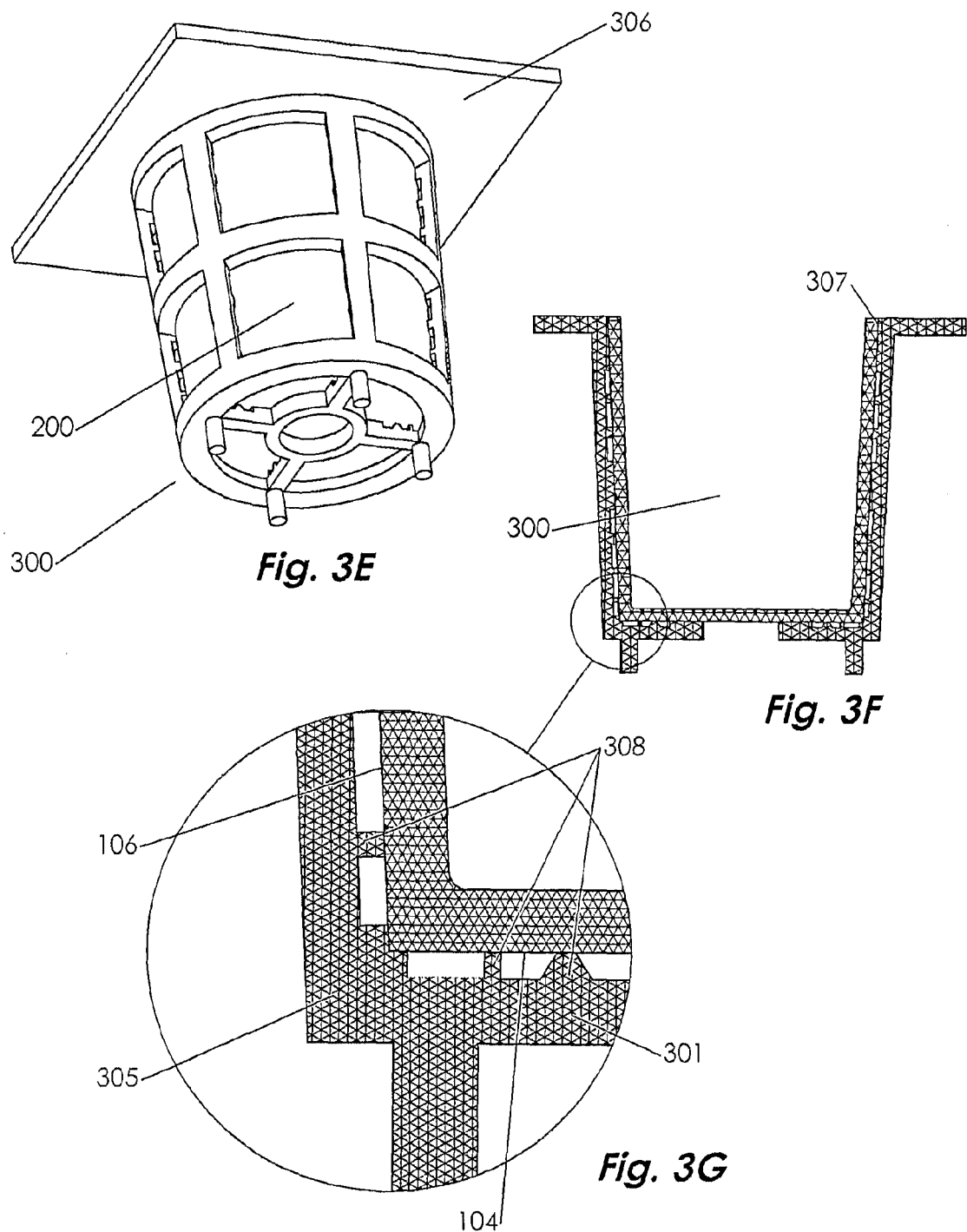

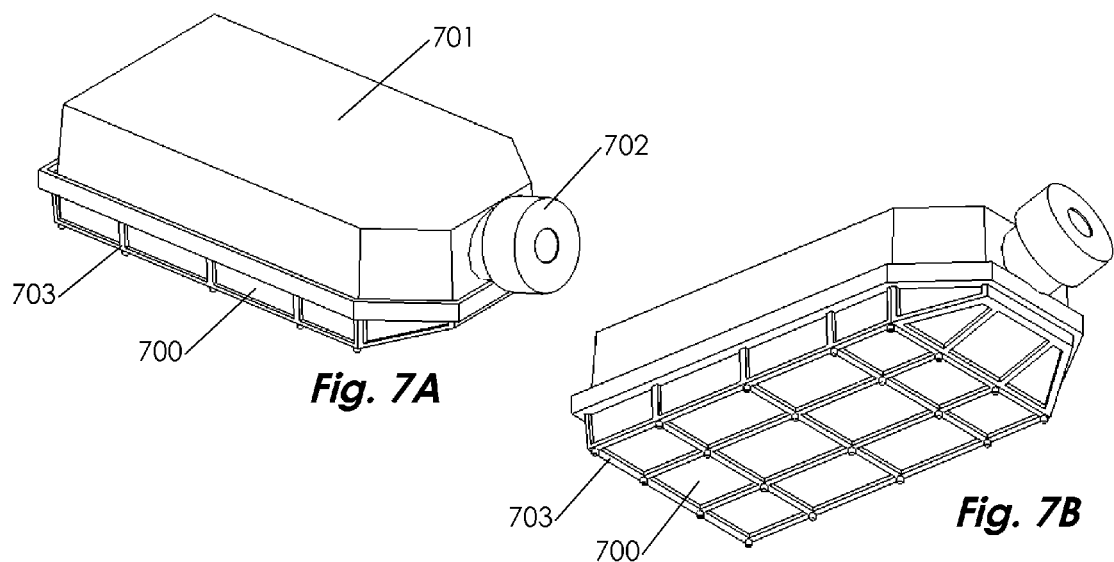
Fig. 7A
Fig. 7B
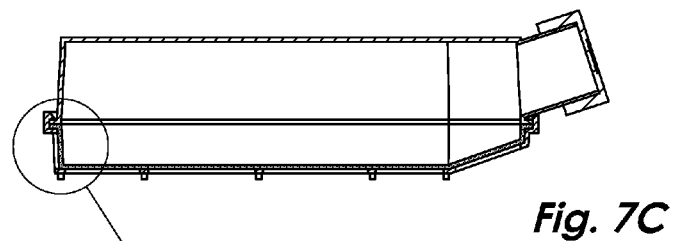
Fig. 7C
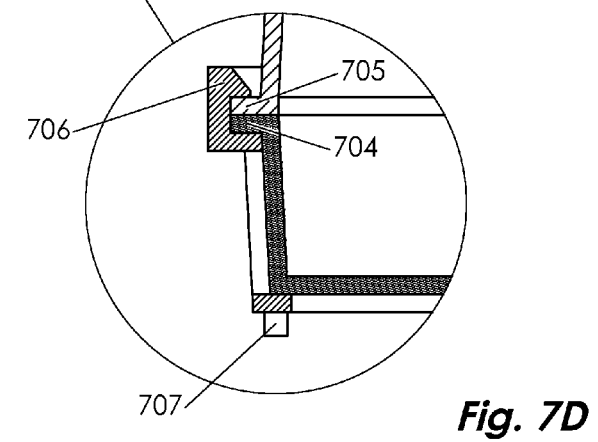
Fig. 7D

| Vessel - Cell Density | ECOD | Sulfonation | Glucuronidation |
|---|---|---|---|
| Control - Density 1 | 48.7 | 42.5 | 2.8 |
| Gas Permeable - Density 1 | 1470.8 | 79.3 | 319.7 |
| Control - Density 2 | 15.8 | 10.7 | 1.8 |
| Gas Permeable - Density 2 | 1489.6 | 51.3 | 369.5 |

Data in units of pmol/min/10e6 cells

CELL CULTURE APPARATUS AND ASSOCIATED METHODS

PRIORITY DATA

This application claims priority from U.S. Provisional Patent Application No. 60/865,797 filed 14 Nov. 2006, which is hereby incorporated by reference.

FIELD OF INVENTION

This invention relates to cell culture apparatus, specifically to gas-permeable cell culture vessels used for growing cells and tissues in vitro. This invention additionally relates to methods of preparation and use of gas-permeable cell culture vessels.

BACKGROUND OF THE INVENTION

Various vessels have been developed which serve to contain and promote the culture of cells taken from animal and vegetable tissues. Such devices include, but are not limited to, dishes, multi-well plates, flasks, and bottles. Typically, these vessels have a substantially flat bottom for the attachment and growth of the cells. The bottom surface is commonly plasma-, flame-, or chemically-treated to enable cell attachment through cellular attachment factors; vessels directly coated with attachment- and growth-promoting biomolecules are also available. Most vessels are disposable and produced from clear polystyrene or other rigid thermoplastic material.

Prior to the advent of plastic cultureware, cells were grown in glass vessels because glass is inexpensive, easy to sterilize, and can be made conducive to cell attachment. Later, cell culture vessels made from injection-molded polystyrene were introduced to capitalize upon this material's low cost, rapid moldability, and clarity. Today, most cell culture vessels continue to be produced using injection-molded polystyrene. The cellular microenvironment of such vessels is generally hypoxic and may require some means of enhancing gas exchange through the media—such as a bubbling apparatus—to prevent the media from becoming $CO_2$-rich and $O_2$-poor and thus depriving the growing cell mass of the gas balance needed for functional metabolic respiration.

Adherent-dependent cells typically become flattened against the growth surface and will generally grow to a confluent monolayer a single cell layer deep. Compared to cells in vivo, cells grown in vitro have compromised metabolic function: Some cell products and surface molecules are not expressed; those that are expressed are often produced in amounts significantly below physiological levels. Additionally, the cells lose their natural morphology and fail to grow into a 3-dimensional mass representative of in vivo tissue. To promote 3-dimensional growth, micro-scaffolds have been developed; yet, such scaffolds are commonly expensive to produce and difficult to apply. Moreover, micro-scaffolds are generally limited in their 3-dimensional capacities since cells internal to the growing cell mass are significantly removed from the perimeter where gas exchange occurs with the growth media. It is notable that, in vivo, cells are on average positioned no more than three cell diameters away from a capillary.

Primary cells—cells cultured from tissues taken directly from an organism—are difficult to grow and have limited longevity. Also, these cells generally require passaging at relatively short intervals: If the cells are not frequently removed from the growth surface, resuspended, split (diluted in cell count per unit volume), and re-seeded into a new culture vessel, the growing cell mass will usually senesce or die within a period of 10 days or less.

BRIEF DESCRIPTION OF THE DRAWINGS

FIG. 3E is a perspective view of a vessel suspended from a lattice structure coupled to or molded beneath a hole in a suspensory element.

FIG. 3F is a front sectional view of a vessel suspended from a lattice structure coupled to or molded beneath a hole in a suspensory element.

FIG. 3G is a detail view of the corner region of the vessel of FIG. 3F.

FIGS. 7A and 7B are superior and inferior perspectives view of a vessel mated to a cap-like upper structure with a snap-fitted support lattice structure.

FIG. 7C is a side sectional view of the vessel, cap, and support lattice of FIGS. 7A and 7B.

FIG. 7D is a detail view of the corner region of FIG. 7C.

Figures 1A, 1B, 1C, 1D:
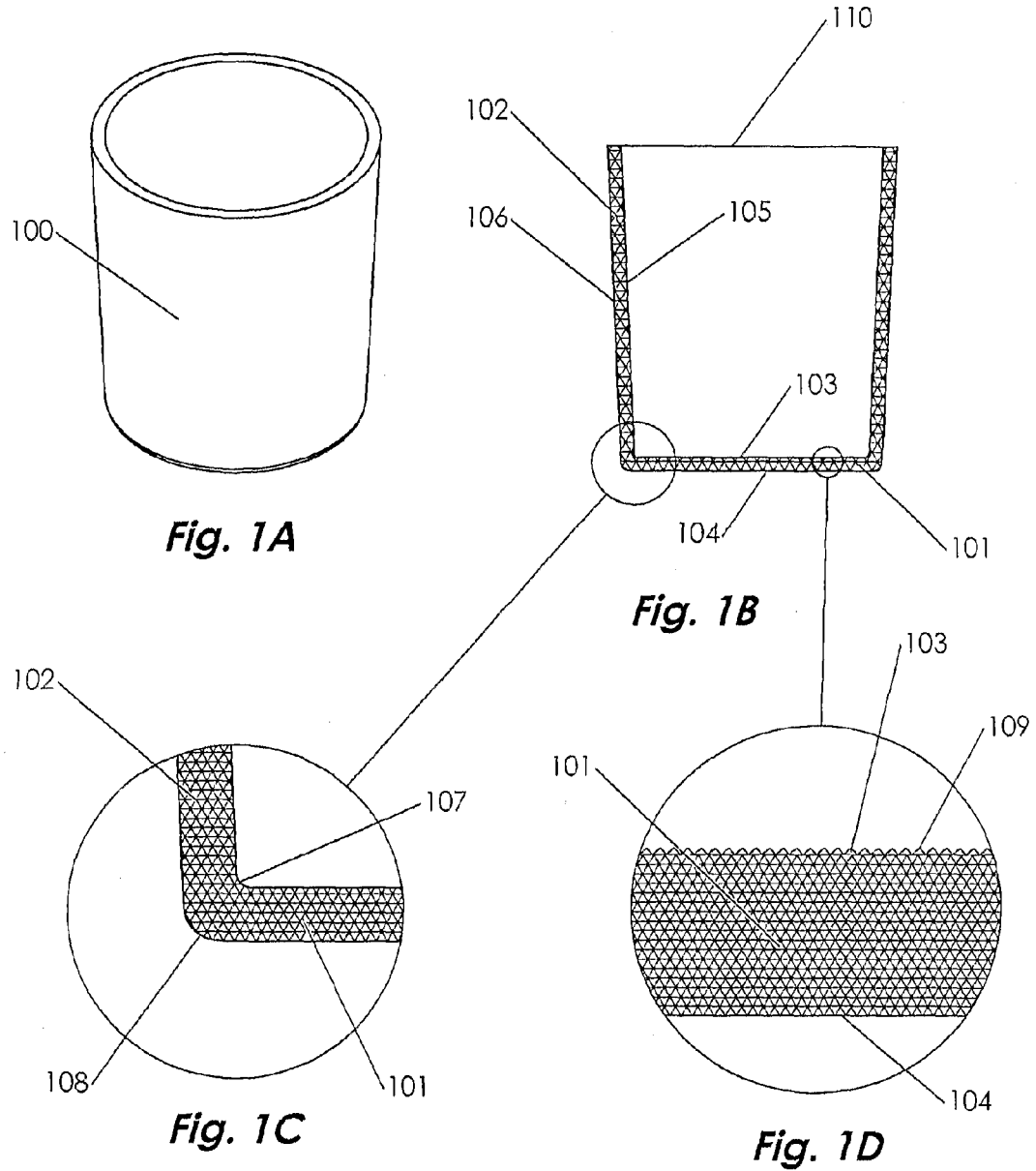
FIG. 1A is a front perspective view of a cell culture vessel, according to my invention.
FIG. 1B is a front midline sectional view of the vessel of FIG. 1A.
FIG. 1C is an enlargement of the front midline sectional view of the vessel of FIG. 1B at the wall-bottom intersection.
FIG. 1D is an enlargement of the front midline sectional view of the vessel of FIG. 1B at the vessel bottom.

| Reference Numerals | |
|---|---|
| 100 | vessel |
| 101 | vessel bottom |
| 102 | vessel sides |
| 103 | bottom inner surface |
| 104 | bottom outer surface |
| 105 | side inner surface |
| 106 | side outer surface |
| 107 | inner bottom-side radius |
| 108 | outer bottom-side radius |
| 109 | surface texture |
| 110 | vessel top orifice |
| 200 | vessel |
| 201 | peripheral flange |
| 202 | suspensory element |
| 203 | thru-hole |
| 204 | supporting surface |
| 205 | multiple-vessel array |
| 206 | vessel top edge |
| 207 | thru-hole inside bore |
| 208 | upper annular flange |
| 208' | lower annular flange |
| 209 | annular groove |
| 300 | standoff frame |
| 301 | bottom support lattice |
| 302 | windows in support lattice |
| 303 | spacer features |
| 304 | standoff frame |
| 305 | lateral support lattice |
| 306 | suspensory element |
| 307 | thru-holes |
| 308 | spacer features |
| 400 | standoff features |
| 401 | lid |
| 500 | multiple-vessel array |
| 501 | suspensory element |
| 502 | legs |
| 503 | lid |
| 504 | vessel top surface |
| 505 | thru-holes |
| 506 | suspensory rack top surface |
| 507 | support surface |
| 600 | multiple-vessel array |
| 601 | suspensory rack |
| 602 | lid |
| 603 | suspensory element |
| 604 | array of thru-holes |
| 605 | suspensory rack side-walls |
| 606 | windows in rack side-walls |
| 607 | upper side-wall |
| 608 | lower side-wall |
| 609 | lid skirt elements |
| 610 | rim |
| 700 | vessel |
| 701 | cover |
| 702 | cap |
| 703 | support lattice |
| 704 | vessel flange |
| 705 | lid flange |
| 706 | snap-fit element |
| 707 | standoff features |

DETAILED DESCRIPTION

Accordingly, several advantages of the present invention are as follows: Firstly, cell culture apparatus has the ability to passively supply the growing cells with a high amount of oxygen and to passively remove excess carbon dioxide through the use of gas-permeable vessels. Secondly, the gas permeable vessels can be treated to promote the adhesion of materials supportive of cell adhesion and growth. Thirdly, the cell-interfacing surfaces of the cell culture apparatus can be fabricated with one or more textures to promote cell adhesion and growth. Fourthly, the cell culture apparatus is designed in a manner so as to be compatible with existing laboratory devices and protocols. Fifthly, the cell culture apparatus is designed such that overall cost and complexity is reduced to allow for economical production and subsequent disposal after single use. Sixthly, the cell culture apparatus can be used to culture a variety of cells, particularly those with high metabolic demands, to very high densities and for prolonged periods with reduced requirement for passaging.

A cell culture apparatus and associated methods are provided. In one aspect, for example, such an apparatus may comprise one or more vessels composed of a gas permeable material having a substantially flat bottom and substantially vertical sides. The vessels are supported by a suspension rack or elevating structure constructed to provide the vessel bottom and sides with maximum access to the adjacent gaseous environment while allowing ease of use, compactness, and manipulation by standard laboratory devices and robotics. Typically, a lid is provided to reduce water loss and prevent airborne contamination of the vessels. A biocompatible coating may be applied to the inner surface of the vessel to provide enhanced cell attachment and growth. Likewise, a defined texture may be added to the cell-interfacing surface of the vessel to promote subsequent cell attachment and growth.

EXAMPLE EMBODIMENTS

FIGS. 1A-1D show an embodiment of the cell culture apparatus in the basic form. The apparatus is composed of a vessel 100 or plurality of vessels in which each vessel comprises a bottom 101 and peripheral sides 102 with an open orifice at the top 110. The bottom is further comprised of an inner surface 103 and an outer surface 104; likewise, the sides also have an inner surface 105 and outer surface 106. The bottom and sides may be connected without transition radii; conversely, the bottom and sides may have an inner radius 107 connecting inner surfaces 103 and 105 and an outer radius 108 connecting outer surfaces 104 and 106. The bottom and sides are molded integrally and are composed of a gas-permeable material. Typically, the bottom and sides of the vessel are molded in a single action and as such are of the same gas permeable material. Alternately, the bottom and sides may be of different gas-permeable materials molded in a two-shot or overmold process. The bottom inner surface 103 is commonly provided with a texture 109 to promote cell adhesion and proliferation; however, a smooth finish may sometimes be preferable for improved clarity or ease of manufacturing. Depending upon the application, it may be beneficial to extend the texture from the bottom inner surface 103, over the inner radius 107 if any, and up the inner side surface 105. In this way, it is possible to extend the culture surface and thereby increase the number of cells cultured per vessel 100.

The periphery of the bottom may be circular, thereby the sides forming a single curved peripheral wall element; alternately, it may be polyhedral, and thereby adjoin to substantially flat faceted peripheral wall elements. The use of a polyhedral bottom—e.g. square, rectangular, or hexagonal—may be beneficial to maximize packing when a plurality of vessels is employed in an array. The peripheral walls are usually substantially vertical but may have draft to assist in de-molding or to allow stacking and nesting. Dimensions of the bottom and sides may be specified as required for various tasks. For example, in the case of a low profile vessel such as Petri dish, the diameter of the bottom is typically less than 200 mm and the height of the sides less than 400 mm. In the case of a multiple vessel array which utilizes a higher profile, the bottom diameter may range from 2 mm to 50 mm while the height of the sides ranges from 5 mm to 50 mm. The junction between the sides and bottom, both inside and outside, is generally provided with a small radius 107 and 108. In the case of the inside junction, this radius may assist with preventing bubble entrapment, particularly during filling. The outside junction is commonly radiused to allow for a smooth wall thickness transition and ease of mold ejection; conversely it may be left unradiused due to mold construction.

The thickness of the culture vessel bottom and sides is of primary importance to its gas permeability: The thinner the wall, the greater the gas permeability. Additionally, a thinner wall leads to greater optical clarity when the material is translucent, as with many silicone and thermoplastic materials. Conversely, the wall thickness must be great enough to provide for the structural stability of the vessel: bowing of the sides and bottom and associated cell disruption can occur if the gas permeable material is soft or elastomeric—such as in the case of silicone—when the wall is too thin. Ultra-thin walls can lead to undue loss of water through the wall via transpiration. In one embodiment of the invention, a wall thickness of 0.1 mm to 3.0 mm is utilized. Another embodiment utilizes a wall thickness of about 0.5 mm to 1.5 mm. In yet another embodiment, the wall thickness of the vessel is about 0.8 mm. For structural, optical, and other reasons, it may be desirable to use different wall thicknesses for the sides and the bottom. For example, it may be suitable to utilize relatively thick sides to achieve good structural rigidity while employing a relatively thin bottom to improve gas permeability and optical clarity. To balance structural integrity with gas permeability, it is possible to provide fluting or groves or ribs the sides, the bottom, or both to achieve thickened regions with increased stiffness and thin regions with enhanced gas permeability. During production, the sides can be marked or embossed with gradations and numbers to indicate specific volumes or fill levels.

The surfaces of both the bottom and the sides are commonly smooth, and may utilize a highly polished finish to enhance viewability. It may however be advantageous to texture the inner surfaces of the bottom or sides to provide the cells with micro- or milli-features on which to adhere and generate traction. Such a texture, or series of textures, may also provide benefits in terms of enhanced gas permeability, enhanced coatability, and enhanced microcirculation of media between the features of the texture. The texture produced by high speed polishing of the mold surface with 400-grit sandpaper is a preferred embodiment; however other textures such as those produced from heavier or lighter grit sandpaper or beadblasting or the use of etched finishes may also be beneficial. Both smooth and textured surfaces are typically applied during molding via the contacting mold surface but may be added post-molding via embossing, solvent polishing, beadblasting, or other method. The inner surfaces of the bottom and the sides may be rendered hydrophilic or hydrophobic by standard means, such as gas plasma or corona discharge, which may promote the adhesion of biocompatible coatings or preferred biomolecules found in the growth media Nitrogenating or oxidizing the growth surfaces using a nitrogen or oxygen gas plasma, respectively, may be particularly helpful in obtaining strong cell attachment. As with the sides, use of gradations, grids, or other markings on the bottom surfaces may assist in cell growth or analysis.

Figure 2A:
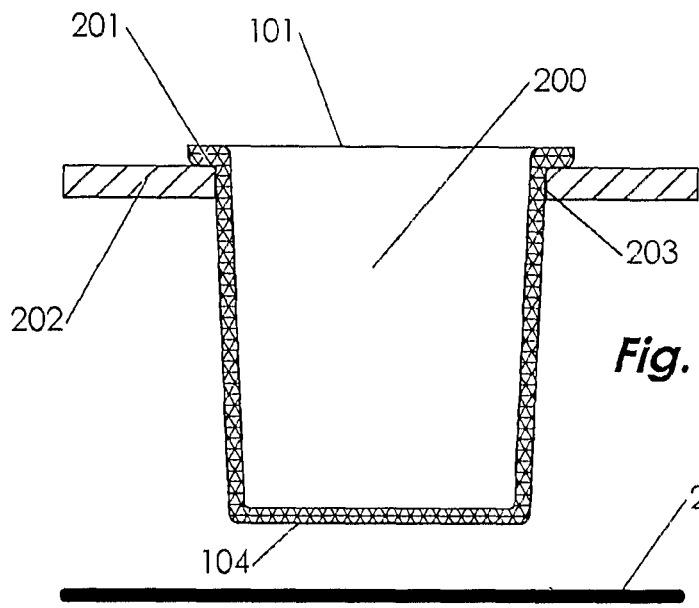
FIG. 2A is a front sectional view of the vessel provided with an annular flange and suspended through a hole in a suspensory element.

FIG. 2A shows an embodiment of the cell culture apparatus in which the vessel 200 is suspended through a hole 203 in a planar suspensory element 202 from an integral external peripheral flange 201 located at or near the top of the vessel orifice 101 on its periphery. Suspensory element 202 is commonly planar or sheet-like; however more substantially 3-dimensional structures may be employed to improve packing of the vessels, prevent cross-contamination, or provide a fluid dam. Flange 201 may be circular, rectangular, or any other geometry conducive to its suspensory function. The suspension of the vessel provides maximum contact of the bottom and side outer surfaces with environmental gases, notably oxygen and carbon dioxide, which diffuse though the gas-permeable material or materials composing the vessel. The hole 203 is typically sized slightly smaller than the diameter of the outer surface of the vessel wall 102 to provide a slight interference fit. The suspensory element 202 is commonly of rectangular geometry and is held at some distance above the supporting surface 204—bench top, shelf, microscope stage, etc.—by the use of legs. These legs may be integral to the suspensory element or may be secondary components added during or after the production of the element. Alternately, the suspensory element may be held above the supporting surface 204 by the use of lateral walls, either integral to the suspensory element—for example, molded continuously with it—or added after production of the element. It is important that the suspensory element be positioned high enough above the supporting surface that the outer surface of the vessel bottom 104 generally maintains a minimum separation distance of 0.5 mm from the supporting surface 204 to allow adequate circulation of environmental gases with that surface, particularly during incubation. This in turn assures adequate gas exchange through the vessel bottom 101. Vessel 200 is commonly molded separately from suspensory element 202, however, it may also be overmolded onto the suspensory element. Conversely, the suspensory element may be overmolded onto the vessel.

Figure 2B:
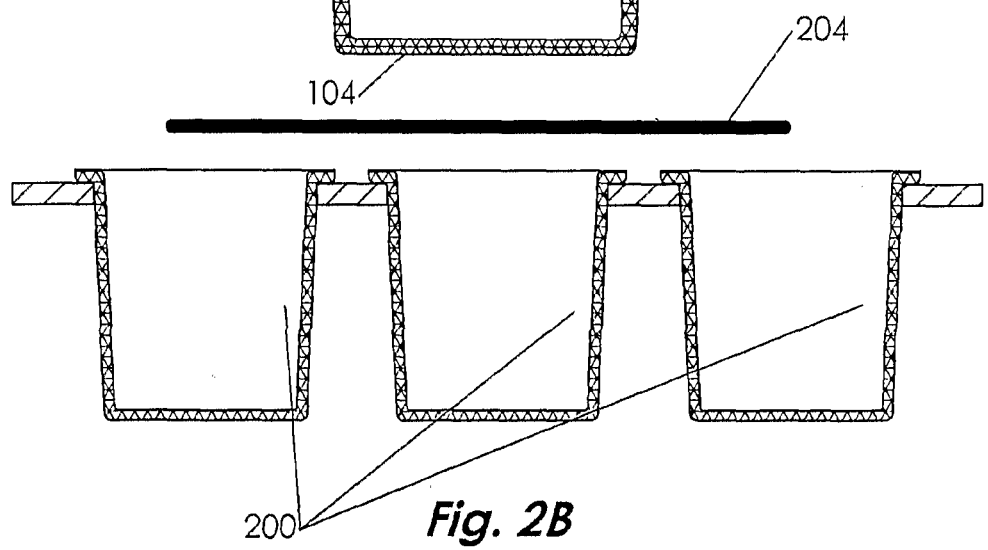
FIG. 2B is a front sectional view of an array of individual vessels with annular flanges suspended from an array of holes through a planar element, connected by a common flange and suspended through holes in a suspensory element.
Figure 2C:
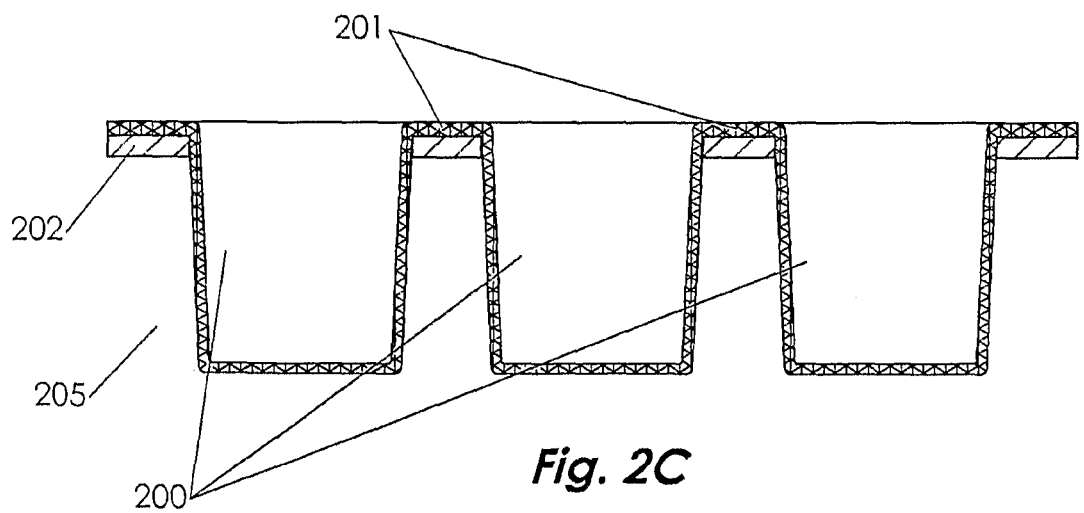
FIG. 2C is a front sectional view of an array of vessels with annular flanges suspended from an array of holes through a suspensory element, the vessels being connected by a common flange.

FIG. 2B furthermore shows an array of the suspended vessels of FIG. 2A. These vessels are discreet items and are thus not connected; such discreet vessels may be molded individually and added individually to the suspensory element 202. Alternately, FIG. 2C shows an array of vessels 200 which are connected by their peripheral flanges 201, thereby resulting in a unitary, multiple-vessel component 205. The connected flanges may either be continuous or may have voids (to reduce the use of material or to provide additional functional elements). The multiple-vessel component 205 may be molded as a single individual part and mated to the suspensory element 202 or it can be composed of several smaller vessel-array elements. The multiple-vessel component 205 is commonly molded separately from suspensory element 202 and thereafter assembled; however, it may also be overmolded onto the suspensory element.

Figure 2D:
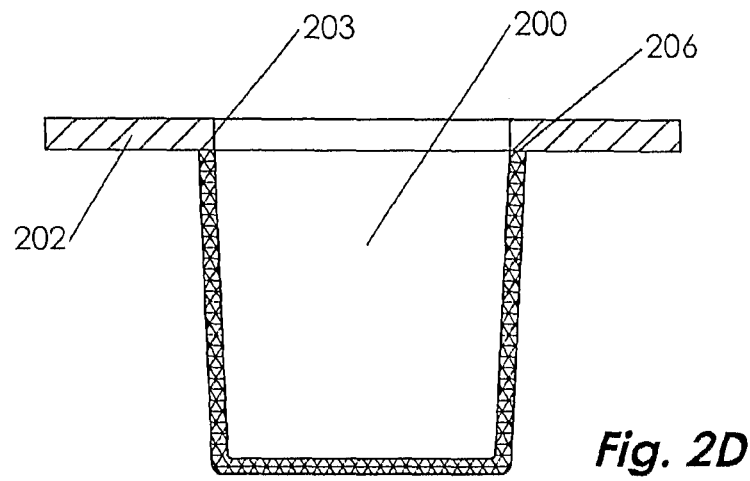
FIG. 2D is a front sectional view of a vessel molded directly onto the lower surface of a suspensory element.
Figure 2E:
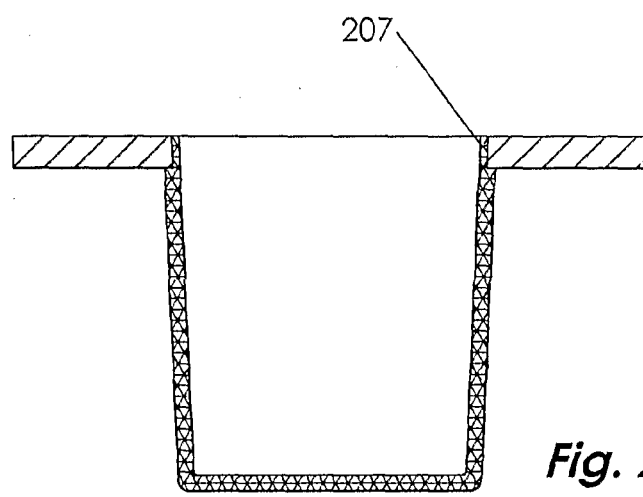
FIG. 2E is a front sectional view of a vessel molded directly onto the lower surface of a suspending element and onto the inside diameter of a through-hole in the suspending element.
Figure 2F:
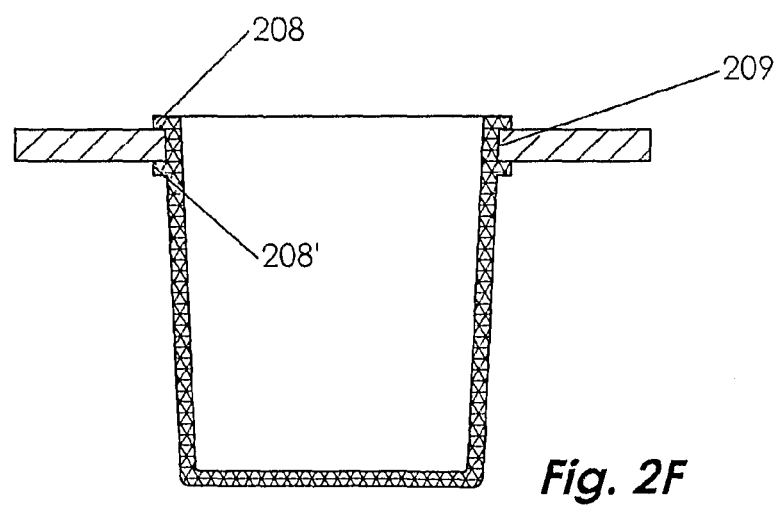
FIG. 2F is a front sectional perspective view of a vessel with double flanges molded directly onto or suspended through a hole in a suspensory element.

FIGS. 2D-2F show an embodiment of the invention in which the vessel 200 is specifically overmolded onto the suspensory element 202. In FIG. 2D, the vessel is molded such that its top edge 206 is directly interfacing the bottom surface of suspensory element 202 and the inside diameters of the vessel 200 and thru-hole 203 are approximately continuous. It may also be desirable to increase the inside diameter of the vessel over that of the thru-hole such that a rim or lid effect occurs. FIG. 2E is similar to FIG. 2D with the added feature of having the inside diameter of the vessel slightly smaller than that of the thru-hole thereby covering 207 the inside bore of the thru-hole and making the inner surface of the vessel continuous with the top surface of the suspensory element. This may serve to coat or passivate the thru-hole surface. In addition to overmolding, the vessels of FIGS. 2D and 2E can be formed separately and attached to suspensory element 202 with an adhesive material. FIG. 2F shows a vessel with upper and lower annular flanges 208 and 208' at the top edge of the vessel and a distance below the top edge, respectively, such that an annular groove 209 is formed in which the edge of the thru-hole is situated. This embodiment provides improved security of fit and may either be implemented by overmolding or by molding the vessel separately from the suspensory element and coupled to it in a subsequent process. It is noted that vessels added secondarily may be beneficial in that the vessel or vessels may be more readily removed from the suspensory element at a later time for visual processing or further analysis. It is also noted that the upper flange is situated on the top surface of the suspensory element and therefore rises above it—this may be beneficial in providing a sealing action wherein the top flange contacts the inner surface of a lid structure; conversely, it may be deleterious if it interferes with proper seating of the lid or with the intended movement of laboratory instrumentation such as a pipetter.

In applications where an array of vessels is employed, it is customary for a vessel's sides to be separated from those of the adjacent vessels to promote air circulation and gas exchange with the cell mass. However, some applications may demand a high degree of space efficiency and thereby require an embodiment in which the sides of adjacent vessels form common walls (e.g., a cellular or honeycomb-like structure). Alternately, there is an embodiment in which the walls of adjacent vessels are common at points or areas (e.g. hexagonal close-packing of cylindrical or hexagonal vessels). These embodiments will reduce overall gas exchange with the cell mass because some or all of the outer wall surfaces of the vessels will not be in contact with atmospheric gas and will therefore provide reduced gas exchange. A worse-case example of this is an "inside" positioned vessel within a multiple-vessel array in which the vessels share common walls. In this situation, only the bottom surface of the vessel is available for atmospheric gas exchange.

FIGS. 3A-3D show an embodiment of the invention in which the vessel 200 is mated to a standoff frame 300. The standoff frame 300 is comprised of a bottom support lattice 301 with one or more windows 302 which provide the vessel with access to environmental gases. Support lattice 301 may be substantially open—i.e., comprised of thin material elements—or may be substantially closed. In either case, windows 302 may be many or few, large or small, regular or irregular depending upon structural requirements, molding issues, and ventilation needs. The standoff frame also includes spacer features 303—e.g., legs, skirts, flanges, bosses—which separate the bottom of the standoff frame 304 from the support surface 204 likewise serving to provide access to environmental gases. Standoff frame 300 may be simply for support of the vessel bottom 101, as in FIGS. 3A and 3B, or may include a lateral support lattice 305, as in FIGS. 3C and 3D, which provide mechanical support with access to environmental gases for the vessel sides. The figures should not limit the geometry or structure of the lattice, which can occur in a wide variety of forms. In both cases, the standoff frame 300 is generally an injection-molded plastic, commonly but not limited to polystyrene, polypropylene, or polycarbonate. The standoff frame may be molded separately from the vessel and coupled to it during a separate operation. Additionally it may be overmolded onto the vessel, or alternately the vessel may be overmolded onto the standoff frame. As with the prior embodiments, the vessel's depth-to-diameter ratio should not be limited by the figures, but should instead be widely definable so as to produce low and wide configurations, deep and narrow configurations, and those in between. As with the prior embodiments, the embodiments of FIGS. 3A-3D may be linked into arrays of vessels supported by a singular standoff frame with multiple "baskets" for the vessels.

Figure 3A:
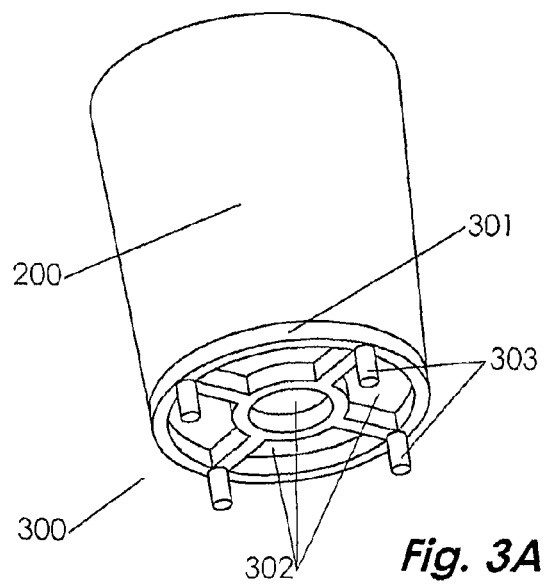
FIG. 3A is a perspective view of a vessel mated to or molded onto an elevating structure.
Figure 3B:
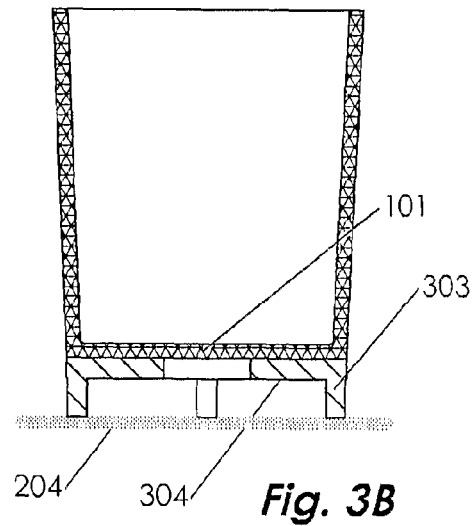
FIG. 3B is a front sectional view of a vessel mated to or molded onto an elevating structure.
Figure 3C:
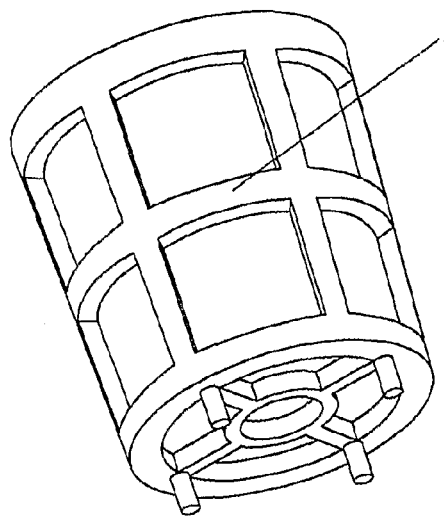
FIG. 3C is a perspective view of a vessel mated to or molded onto an elevating structure having lateral support features.
Figure 3D:
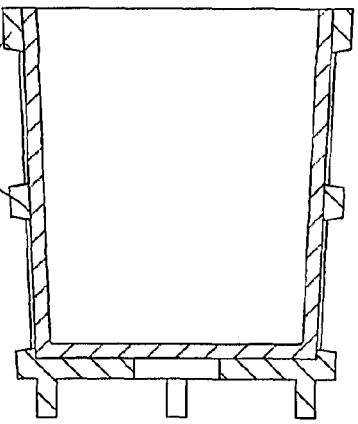
FIG. 3D is a front sectional view of a vessel coupled to or molded onto an elevating structure having lateral support features.

FIGS. 3E-3G depict a standoff frame 300 supporting a vessel 200. Similar to FIG. 2A, this embodiment employs a suspensory element 306 with thru-holes 307 which are then provided with a suspensory frame 300 comprised of a suspensory element 306, bottom support lattice 301, and lateral support lattice 305. FIG. 3G is a detail view of the sectional view of FIG. 3F showing how spacer features 308 may be added to the interior aspects of the suspensory frame 300. These spacer features 308 provide the outer vessel surfaces 104 and 106 with additional access to environmental gases, thereby promoting gaseous exchange with the interior of the vessel and the growing cell mass. Such spacer features may also be applied to the embodiments of FIGS. 3A-3C. The geometric possibilities of the spacer features 308 should not be limited by the figures but instead may be comprised of legs, ribs, and bosses of various shapes and sizes.

Figure 4A:
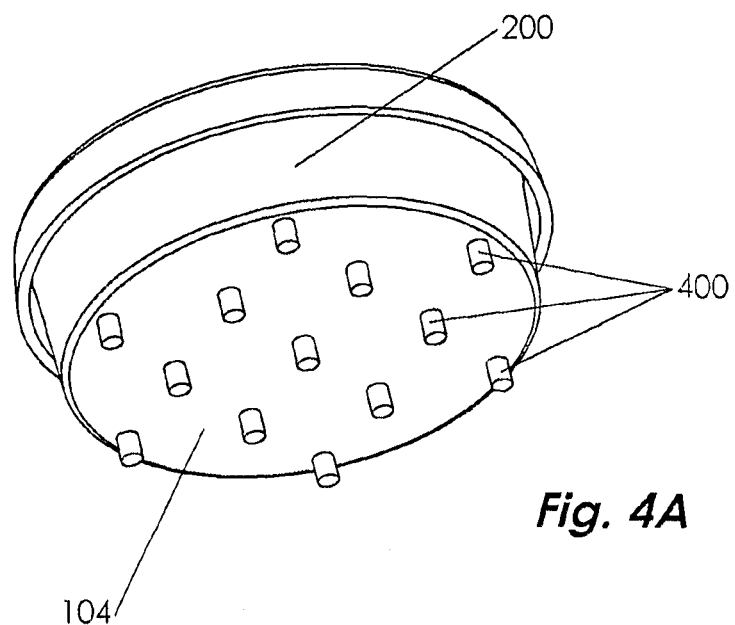
FIG. 4A is a perspective view of a vessel with integral stand-off elements and a lid.
Figure 4B:
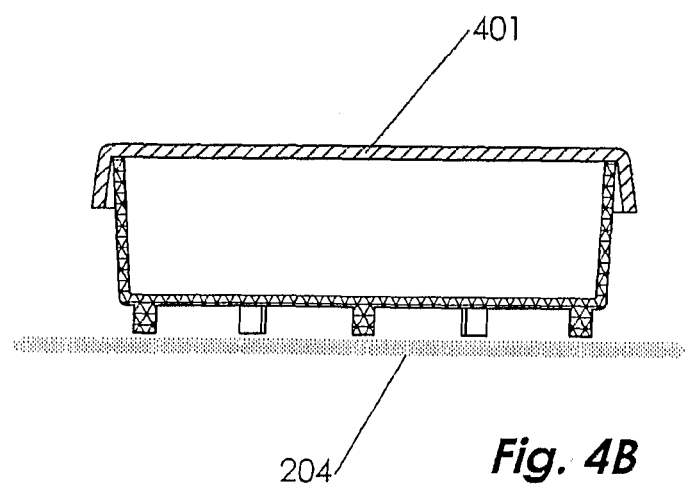
FIG. 4B is a front sectional view of the vessel of FIG. 4A.

FIGS. 4A and 4B show an embodiment of the system in which standoff features 400 are provided which are integral to the outer bottom surface 104 of vessel 200. Standoff features 400 may be molded simultaneously with the vessel and thereby be composed of the same material as the vessel 200. Alternately, the standoff features may be composed of a different material and may be overmolded onto the outer bottom surface 104 of vessel 200 or produced separately and coupled during a separate operation. As with the embodiments in FIGS. 3A-3D, the standoff features serve to separate the vessel bottom 101 from the support surface 204 to provide access to environmental gases. Also shown is a lid 401 to prevent ingression of contaminants into vessel 200 and reduce evaporation of fluids from the cell growth medium. Such a lid may also be an additional component of the prior embodiments and may take various forms including but not limited to planar, planar with skirt, circular, rectangular, or polyhedral.

Figure 5A:
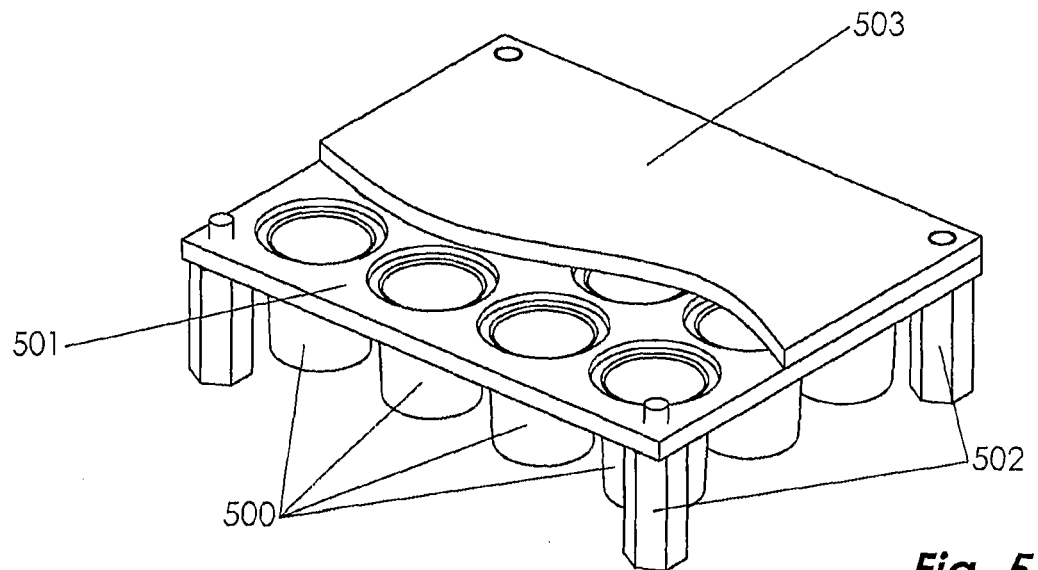
FIG. 5A is a perspective view of an array of vessels in a rack assembly comprising a suspensory element, legs, and a lid.
Figure 5B:
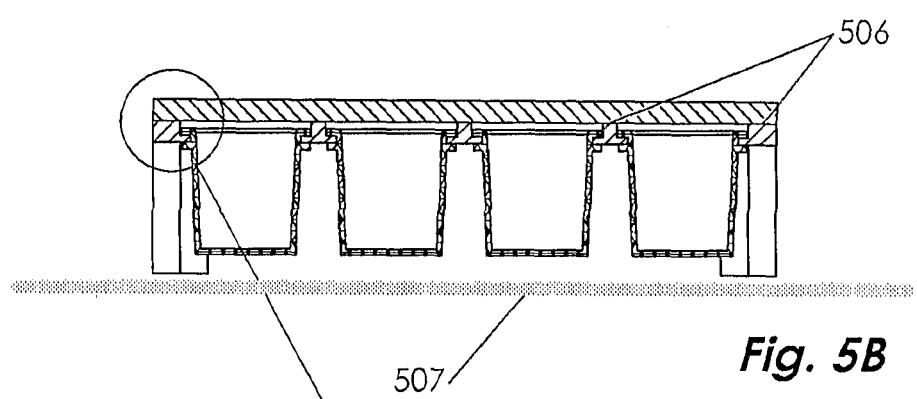
FIG. 5B is a front sectional view of the vessels and rack of FIG. 5A.
Figure 5C:
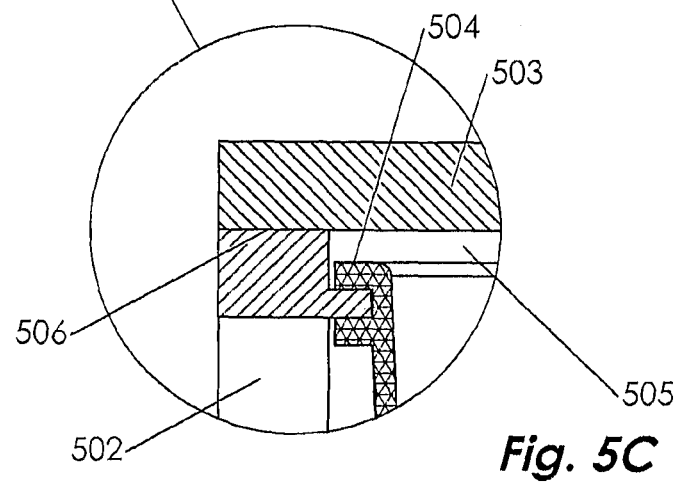
FIG. 5C is a detail view of the corner region of FIG. 5B.

FIGS. 5A-5C show an embodiment comprising a multi-vessel array 500, suspensory element 501 with legs 502, and planar lid 503 (lid shown cut-away for viewing purposes only). To avoid potential contamination from the lid 503 contacting the top surface of the vessel 504, the thru-holes 505 in the suspensory element may be provided with a counter bore, this bore being sufficiently deep and wide to allow the top suspensory flange of the vessel to be positioned within the counterbore beneath the top surface 506 of the suspensory rack and thereby separated from the lid 503. This embodiment also may employ a double flange vessel similar to that embodied in FIG. 2F; additionally, a single-flange or overmolded design may be employed. An alternate embodiment uses no counter bore on the thru-holes. In this case, the lid may rest directly on the top surface of the vessel 504 thereby providing a positive seal. Legs 502 are threaded or snap-in standoffs with sufficient length to allow a minimum separation distance between the vessel bottom 506 and support surface 507 of approximately 0.5 mm. The primary advantage to this embodiment is that the suspensory element 501 and lid 503 can be readily produced from pre-cut plastic sheet stock using manual and NC machining; no injection molding in required. It is therefore especially suitable for proof-of-concept and test marketing. As with prior embodiments, the array of vessels 500 may be individual vessels, multiple strip arrays of vessels (e.g., 4×1 or 3×1), multiple small arrays (e.g., 2×2), or a single large array (in this case, 3×4). Likewise, these vessels may be coupled secondarily or may be overmolded.

Figure 6A:
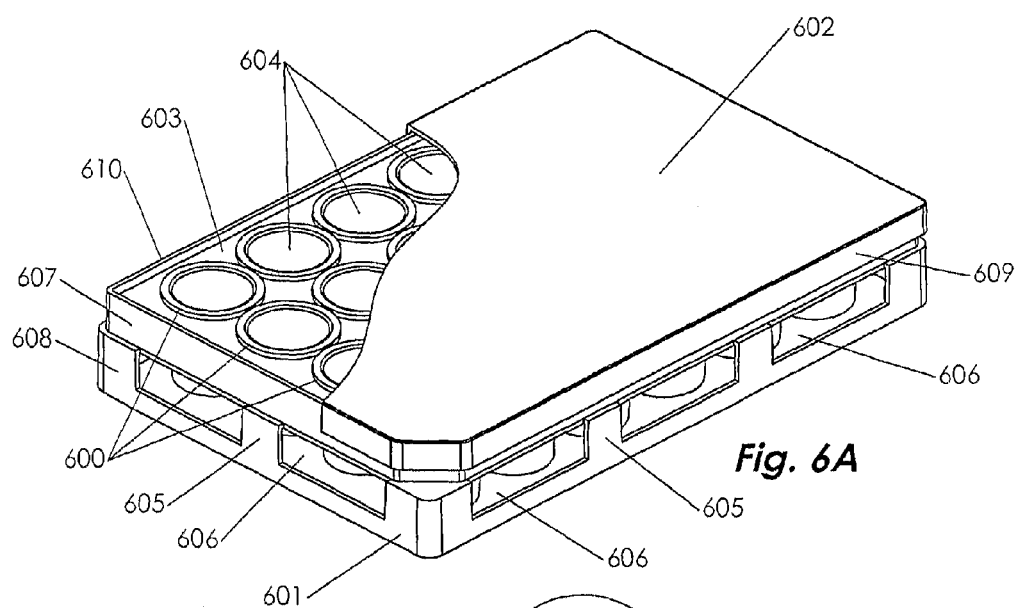
FIG. 6A is a perspective view of an array of vessels in a rack assembly comprising a suspensory element, peripheral walls with a skirt and vents, and a lid.
Figure 6B:
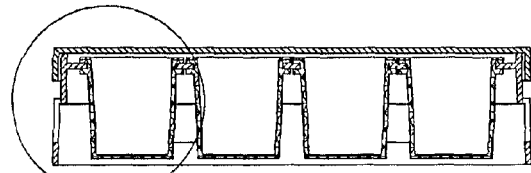
FIG. 6B is a front section view of the vessels and rack of FIG. 6A.
Figure 6C:
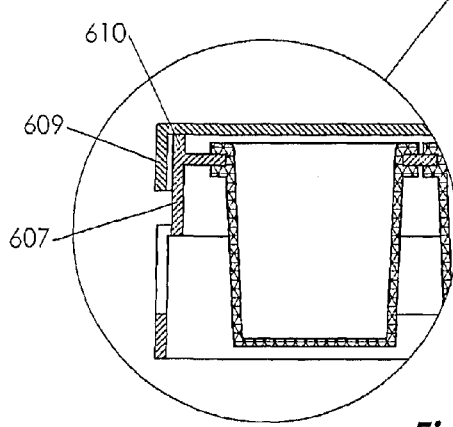
FIG. 6C is a detail view of the corner region of FIG. 6B.
Figure 8:
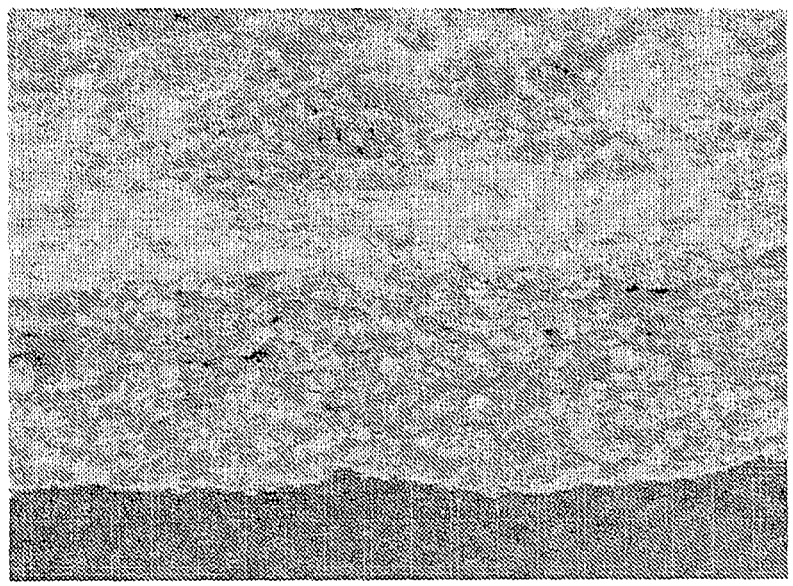
FIG. 8 is an electron micrograph, perspective view, of Hep G2 cells at 8 weeks, grown according to Example 1 (SEM, 350×, isometric-view, fractured edge is visible). Cell mat is approximately 10-15 cells thick. Note spherical cell morphology and copious amounts of extracellular matrix produced by the growing cells.

FIGS. 6A-6C show an embodiment comprising a multi-vessel array 600, suspensory rack 601, and lid 602 (lid shown cut-away for viewing purposes only). Suspensory rack 601 comprises a suspensory element 603 having an array of thru-holes 604 through which an array of vessels 600 is suspended. As before, vessel array 600 may be composed of individual vessels or may be a unitary component. Suspensory rack 601 additionally comprises side walls 605, the number of side walls corresponding to the geometry of the suspensory element. One or more windows 606 are positioned through the side walls, these windows providing vents for environmental gases to freely circulate around the outside of the suspended vessels. Side walls 605 may be formed of a continuous planar structure or may be discreet segments or regions connected by "steps" in the wall; if two segments are employed, the upper segment may be considered the upper side wall 607 while the lower segment may be considered the lower side-wall 608. The employment of two-segment outer walls for such multi-vessel rack structures is common in the art. As with prior embodiments, the vertical position of the suspensory element 603 is sufficient to maintain a minimum separation distance of 0.5 mm between the outer bottom surface of the vessels and the supporting surface. As before, if this separation distance is too large, problems with imaging the cell mass with a microscope may arise; if too small, insufficient gas circulation beneath the vessel bottom and the supporting surface may occur.

The thru-holes 604 in suspensory element 603 may, as with the prior embodiment, be counter bored. Alternately, as shown in FIG. 5, the thru-holes may simple (not counter-bored). In this configuration, it is common to provide a short rim or fence 610, this fence commonly being continuous with upper side wall 607 and extending a sufficient distance above the upper surface of the suspensory element to prevent the lid 602, when seated, from contacting the tops of the vessels. It is noted that the lid 602 may be seated directly on the top face of the rim 610, or may be offset from the lid using small ribs or standoff features (not shown) to promote ventilation. Ventilation may also be enhanced by employing a discontinuous rim. Because the vessels are aerated through their bottoms and sides (and therefore not necessarily required to be ventilated from the top of the vessel), direct seating of the lid on a continuous rim structure may provide the benefit of greater resistance to microbial ingression and contamination.

Lid 602 is generally planar and shaped to correspond with the top outline of the rack. However, lid 602 may also be substantially 3-dimensional to allow for alternate functions. Skirt elements 609 protrude in a generally perpendicular direction to the plane of the lid and are generally continuous around the periphery of the lid. Generally, the vertical dimension of the skirt element is small enough to avoid interfering with the step between the upper side walls and the lower side walls of the rack.

The suspensory rack 601 and lid 602 may have corresponding corner notches, radii, or chamfers to confer orientation of the lid with the rack. Though not shown in the figures, suspensory rack 601 and lid 602 may include ribs, bosses, and other secondary features to provide added benefits such as stiffness, positioning, ventilation, and stacking.

FIGS. 7A-7D show a flask-like embodiment comprising a single gas permeable vessel 700, mated to a rigid cover 701 with cap 702 using a support lattice 703. Typically, cover 701 and support lattice 703 are molded from stiff, transparent materials such as polystyrene or polycarbonate however other materials may also be used. As shown in FIGS. 7C and 7D, flanges 704 and 705 may be positioned on the peripheral edges of the vessel component, the cover component, or both. In the embodiment shown, both vessel and cover have peripheral flanges which mate in a face-to-face fashion. Additionally, the contacting faces of flanges 704 and 705 may be provided with short rib structures to provide enhanced sealing capabilities. Support lattice 703 may be provided with snap-fit elements 706 which function to mechanically mate peripheral flanges 704 and 705. This embodiment works well if the gas permeable vessel 700 is composed of a soft or elastomeric material such as silicone rubber. It may also provide the advantage of a reversible fit, allowing the cover and vessel to be disassembled and thereby providing direct access to the cell mass. Alternately, peripheral flanges 704 and 705 may be directly bonded using adhesive, or nonadhesively with some type of thermal technique such as but not limited to ultrasonic welding, vibration welding, or radio-frequency welding.

To promote ventilation of environmental air around the exterior walls and bottom of the vessel, support lattice 703 may be provided with standoff features 707, which may be—but are not limited to—various geometries including legs, ribs, flanges, or bosses. As shown in the present embodiment, the openings in the support lattice 703 are of a rectangular geometry; other geometries including—but not limited to—circles, polyhedrons, and irregular forms may be employed. Cap 702 is generally secured to lid 701 with a screw (threaded) fit; however other means of securing may be used. Cap 702 may be vented or non-vented, as is commonly employed in conventional T-flask cultureware.

Gas-Permeable Vessel Materials

The material comprising the vessel bottom and sides are of primary importance in promoting gas permeability and thus the growth and metabolic characteristics of the cells.

A preferred type of material is silicone, also referred to as silicone rubber, silicone polymer, SiR, polydimethyl siloxane, PDMS, and VMQ. The permeability coefficient of a material is a determination of how much transmission of a specific molecular species occurs through that material under defined conditions. The permeability coefficient of a material is given in terms of (quantity of molecular species×material thickness)/(area×time×pressure drop across material). The permeability coefficients of $O_2$ and $CO_2$ through silicone are approximately 367 and 2430 [×$10^{-13}$ $cm^3$×cm/($cm^2$×s×Pa), at 0 C], respectively. In contrast, the permeability coefficients of $O_2$ and $CO_2$ through polystyrene at 25 C in the units given above are approximately 2.0 and 7.9, respectively (see for example, Pauly, S. (1989). Permeability and Diffusion Data. In: J. Brandrup, & E. H. Immergut (Eds.), *Polymer Handbook*, $3^{rd}$ *Edition* (pp. 435-449). New York: Wiley-Interscience, which is incorporated by reference). Therefore, silicone has approximately 184× and 308× higher $O_2$ and $CO_2$ permeability, respectively, as compared to polystyrene. Alternative gas-permeable materials include but are not limited to:

Modified Silicone Polymers
poly[1-(trimethylsilyl)-1-propyne]
poly(dimethyl silylmethylene)
other alkyl siloxanes (such as [—Si$(CH_3)_2$RO-], [—Si$(CH_3)_2$XO-], [—Si$(C_6H_5)_2$RO—], [—Si$(CH_3)_2$$(CH_2)_m$—], [—Si$(CH_3)_2(CH_2)_m$—Si$(CH_3)_2$O—], and [—Si$(CH_3)_2$—Si$(CH_3)_2$ $(CH_2)_m$—Si$(CH_3)_2$O—] where R is an n-alkyl group and X is an n-propyl group, m is an integer $\geq 0$).
fluoro-siloxanes (such as the [—$CF_2]_x$—H] functionalized siloxanes Tris(F), Di(F), Mono(F), and F(Si), (Bausch and Lomb Inc., Rochester, N.Y.))
Thermoplastics and Hydrogels
hydroxyethyl methacrylate (HEMA)
polypropylene (PP)
low density polyethylene (LDPE)
polymethylpentene (PMP)
polyoxyphenylene (PPO)
ethyl cellulose (EC)
Rubbers
polybutadiene
polyisoprene (natural rubber)
Inorganics
zeolites
silicates
Composites
silicone+silicalite mixed matrix Additionally, otherwise low permeability polymers, including polytetrafluoroethylene, polycarbonate, polyamide, and various cellulosic materials, can be made gas permeable by the creation of micropores via etching, ion/electron bombardment, spinbonding, differential solvent extraction, or biaxial stressing, which thereby produce pores or voids and thus promote enhanced gas transfer. Similarly, effective side and bottom thickness may be reduced by foaming the base material. However, in the preferred embodiment, solid silicone is employed due to availability, moldability, cost, sterilizability, and acceptable optical clarity, in addition to its superior gas permeability.

Bioactive Coatings

Although one embodiment of the present invention provides for cell growth directly upon a smooth or textured gas permeable material, other embodiments of the invention make use of adsorbed coatings on the vessel inside surfaces to enhance cell attachment and growth. Such coatings are well known in the art and may be composed of single or multiple ECM constituents, proteins, polyamino acids, glycosaminoglycans/proteoglycans, polysaccharides, and other biological compounds. However, due to hydrophilic-hydrophobic repulsion between the coating molecules and the gas permeable material, the surface to be coated often requires an activation step to functionally accept the coating. Common activation processes include but are not limited to corona discharge, plasma discharge, flame treatment, or chemical treatment with a strong acid or base. Covalent bonding with the coating material can be achieved using linking intermediates such as silanes. Other methods of providing bioactive coatings on cell growth surfaces—covalently bonded or adsorbed—are well known in the art.

For example, an embodiment and method for growth surface preparation for hepatocytes utilizes a silicone gas-permeable vessel coated with gelatin. The coating is applied in a solution of 0.75 ug/mL gelatin in phosphate buffered saline (PBS) in a quantity sufficient to provide 2.0 ng of gelatin per square mm of coated surface. The vessel and coating solution is autoclaved at 260° C. for 20 min, thereby sterilizing the vessel as well as promoting coating efficiency, and then incubated overnight in a humidified incubator at 37° C. The remaining coating solution is then removed by pipette and the vessel rinsed 3× with deionized water. Immediately, cells are seeded at $10^5$ cells/well in modified William's E medium with sodium bicarbonate prior to incubation at 37° C. in a 5% $CO_2$ and humidified atmosphere.

To avoid the autoclave step as specified in the prior method, an alternative method may be used. In this method, the gelatin coating material is dissolved in PBS+media to a concentration of 0.75 ug/mL and placed in the vessel to a density of approximately 2.0 ng of gelatin per square mm. The vessel is then incubated for 12 hours at 37° C. in a 5% $CO_2$ and humidified atmosphere incubator. Following this, the cells are seeded at $10^5$ cells/well directly into the vessel (without removing the coating solution) prior to incubation.

Another method has been developed which allows bulk coating of vessels. According to this method, less concentrated coating solution (0.1 ug/mL) is prepared with distilled water in a large beaker (250 mL). Clean vessels are immersed in the solution and left to stand 2 min to 24 hrs or more depending upon the amount of coating material to be applied. The vessels are then removed with tweezers and excess moisture is shaken off. The vessels are placed in racks and dried before use. The vessels and rack can then be packaged and sterilized via standard means including autoclave, EtO, gamma radiation, or e-beam.

A spray-on coating method has been developed to reduce the time required to coat the vessel. A concentrated coating solution (0.1 mg/mL) is prepared in distilled water and placed in a clean airbrush reservoir bottle. The outlet nozzle of the airbrush is adjusted to give more air than solution as judged by the pin in the nozzle being visible about 3 mm beyond the opening. The coating solution mist stream is pointed in a cleaned and dried vessel until the bottom surface is visibly covered with microbeads of moisture. The vessel is then autoclaved (20 min) and dried (30 min dry heat cycle in autoclave) prior to storage or seeding with cells.

In conclusion, it can be seen that, according to the invention, a Cell Culture Apparatus and Associated Methods is provided which can significantly increase the quantity, quality, and duration of cells in culture, and also allow multilayered cell growth of normally contact-inhibited cells, yet can be produced in an affordable, reliable, and standardized manner. As stated, the Apparatus can be produced from a variety of gas permeable materials including silicone and related polymers. It can be produced in single- or multiple-vessel configurations. It can be produced as a stand-alone device or can be produced in conjunction with a rack or other support system. The growth surfaces of the Apparatus can be molded with one or more textures. The growth surfaces of the Apparatus can be treated using one or more physical- or chemical-based methods to increase coatability. Furthermore, the growth surfaces of the Apparatus can be coated with one or more bio-active coatings, such coatings being commonly composed of extracellular matrix constituents.

While the description above contains many specificities, these should not be construed as limiting the scope of the invention but as merely providing illustrations of some of the presently preferred embodiments and formulations of this invention. Various other embodiments, formulations, and ramifications are possible within its scope. For example, while the various embodiments are depicted as having a generally well-like form, it may also be suitable to utilize other forms such as roller bottles, cylinders, or bags. Other embodiments can contain additional features such as splash pads, multiple chambers, and fluid paths for enhanced usability and performance.

Thus the scope of the invention should be determined by the appended claims and their legal equivalents, rather than by the examples given.

EXAMPLES

Example 1

Viable Multilayer Growth of Hep G2 Cells without Passaging

Figure 9:
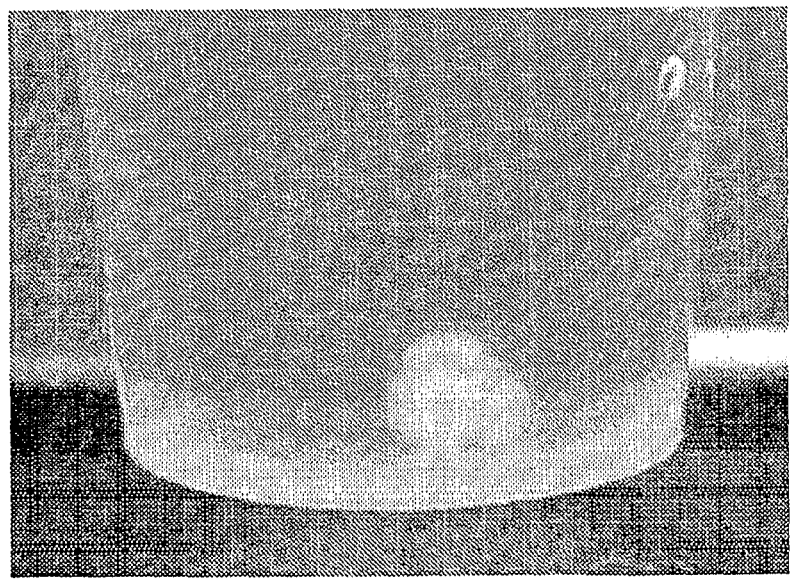
FIG. 9 is a digital photograph of NIH 3T3 cells (mouse fibroblast), at 2 weeks, according to Example 2 (Side-view photograph, inside diameter of well is 10.5 mm). Cells have grown into white globular mass with fibrous strands attaching to vessel inner walls.

Hep G2 cells (human liver carcinoma) were cultured to approximately 12 cell layers deep for a period of over 180 days without passaging (note: In conventional TC-treated polystyrene labware these cells normally grow to monolayer confluence with various small multilayered foci; passaging is typically required every 3 to 4 days to avoid senescence/cell death). The cells were cultured in a vessel with an inside diameter of approximately 13.5 mm, an inside depth of approximately 17.0 mm and a wall thickness of approximately 0.75 mm, composed of compression-molded medical-grade silicone, Shore A40 durometer (Med-4940, NuSil Technologies, Carpinteria, Calif.). The mold surface which formed the inner bottom surface of the vessel was textured using 400 grit sandpaper, applied using a lathe. The mold surface which formed the outer bottom surface of the vessel was highly polished. After molding, the vessel was cleaned using a five-minute soak in 2% Alconox® in warm tap water followed with 3 rinses in tap water and 3 rinses in distilled water. A bioactive coating was produced by dissolving porcine Type-1 gelatin in phosphate buffered saline (PBS) to a stock concentration of 1 mM (10 mgs/ml). This solution was further diluted to 0.75 ug/mL and was used to coat the bottom surface of the vessel by pipetting 0.4 mL into each vessel (2.0 ng coating material per mm of coated vessel surface). Vessels were previously placed in a polycarbonate rack with through-holes and suspended using a top annular flange on the vessel; the rack also has a flat cover and four nylon legs which permit good air circulation around one or more suspended vessels. The rack and vessels with coating solution were placed into an autoclave and autoclaved for 20 min at 260° C. After cooling in the autoclave, the rack and vessels is removed and placed in an incubation oven at 37° C., 5% $CO_2$, and 95% humidity for at least 12 hours. The rack and vessel is then removed and the coating solution is removed from the vessel using a pipette and rinsed once with 0.4 mL phosphate buffered saline (PBS). Hep G2 cells are then seeded into the well at a density of 3,000 to 500,000 cells/vessel using DMEM:

The medium is exchanged every 1-2 days; when changing medium, 0.1-0.2 ml is left behind in the vessel at each interval to reduce fluid turbulence on the growing cell mass. FIG. 9 is a scanning electron micrograph of a vertical fracture surface of a cell mass grown in culture for 8 weeks.

Example 2

Multilayer Growth of NIH 3T3 Cells without Passaging

Figure 10:
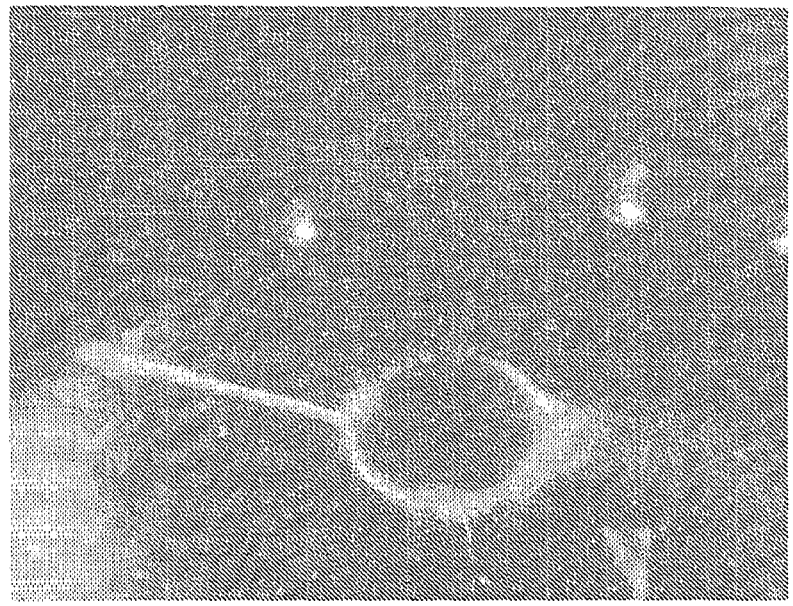
FIG. 10 is an optical stereomicrograph, perspective view, of NIH 3T3 cells at 7 weeks, according to Example 2. Globular structure on well bottom is attached via cellular strands to vessel wall. Vessel bottom is covered with dense mat of cells. Note cellular character in halo around globular structure.
Figure 11:
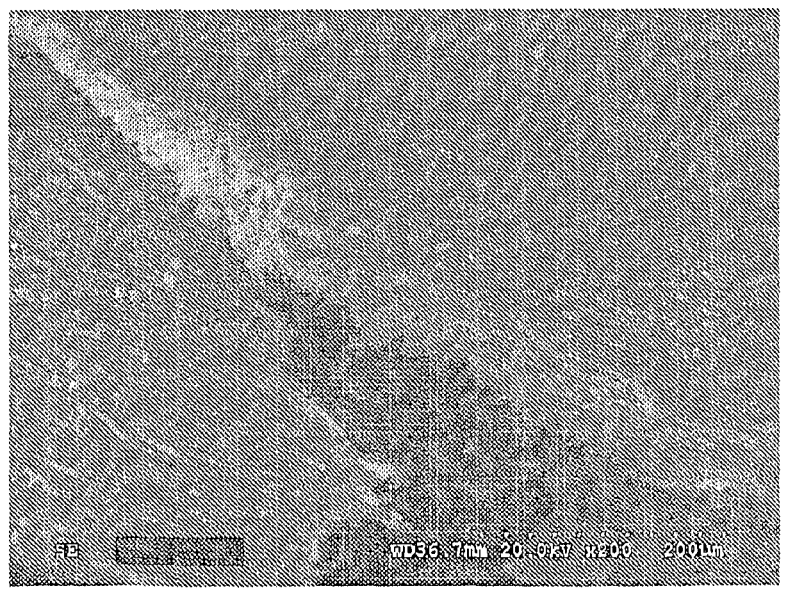
FIG. 11 is a scanning electron micrograph, perspective view, of NIH 3T3 cell culture at 6 weeks, according to Example 2. Typical fibroblast bipolar cell structure is exhibited within the tissue mat covering the entire vessel bottom. Note presence of multilayers on fraction face.

NIH 3T3 cells (embryonic mouse fibroblast) were cultured into complex 3-dimensional structures for a period of over 4 months without passaging (note: In conventional TC-treated polystyrene labware these cells are normally highly contact inhibited and grow just to monolayer confluence prior to senescence; passaging is typically required every 3 to 4 days to avoid senescence). The vessel geometry and preparation is the same as Example 1. Similarly, the coating material and its application is the same as Example 1. NIH 3T3 cells were seeded at a density of 100,000 cells/vessel. An enhanced media formulation specific to this cell line is used and media is replaced and replenished on a 3-day cycle. After growing to confluence and then into multilayers, the cells commonly form large globular aggregates which can be seen with the naked eye. Fibrous cellular structures typically emanate from the globular aggregates, often connecting through the medium to the vessel inner wall. FIGS. 9, 10, and 11 are, respectively, a digital photograph, optical stereomicrograph, and scanning electron micrograph of NIH 3T3 cells at five weeks post-seed.

Example 3

Viable Multilayer Growth of HEK Cells without Passaging

HEK 293 (adenovirus transformed human embryonic kidney) can be grown to high densities using the above described vessel and surface coating, DMEM media, and seeding densities of 3,000 to 1,000,000 cells/vessel.

Figure 12:
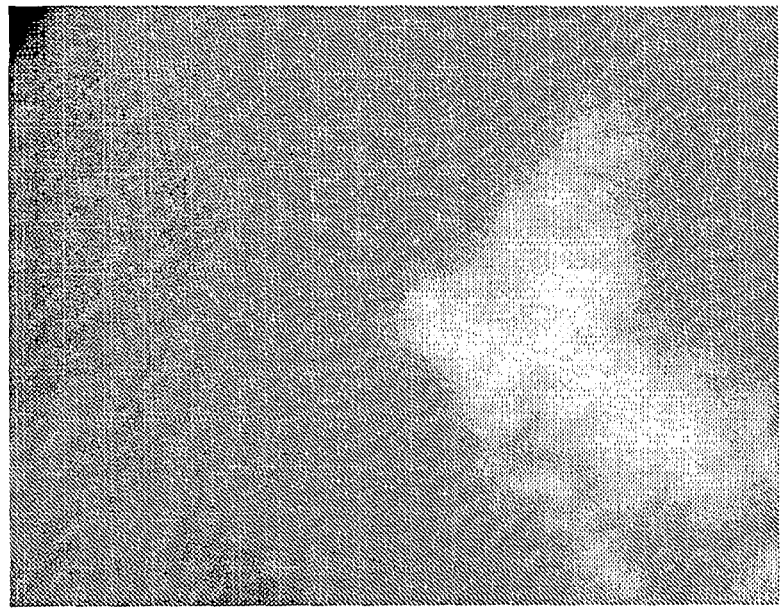
FIG. 12 is an optical micrograph, top view, of HEK 293 cells (adenovirus infected human kidney), according to Example 3. Note dark areas of dense, multilayer growth.

FIG. 12 is an optical micrograph showing dense 3-dimensional growth of HEK 293 cells grown in the above described conditions for 5 days Example 4

Viable Multilayer Growth of Primary Rat Hepatocytes

Primary Rat Hepatocytes (PRH) were cultured to approximately 5 cell layers deep for a period of over 4 weeks prior to passaging. The cells were cultured in a vessel prepared as per Example 1. PRHs were prepared as follows: Cells are harvested from 200-250 gm male Sprague-Dawley rats according to the procedure of Saad, et al. (Saad, B., Schawalder, H. P. & Maier, P. (1993), *In Vitro Cell. Dev. Biol.* 29A, 32-40, which is incorporated by reference). During the harvest procedure, the rat is anesthetized by injection of Avertin (300 mg/kg) and toe and nail pinch used to determine when they have reached the surgical plane of anesthesia. The liver is perfused with a solution of collagenase during deep anesthesia, followed by removal of the liver. The tissue is then homogenized and hepatocytes isolated by differential centrifugation over 9000-30000×g. Hepatocyte suspensions are then prepared by the method of Berry and Friend (see for example, Berry, M. N. and Friend, D. S. (1969). High-yield preparation of isolated liver parenchymal cells: A biochemical and fine structural study. *J. Cell Biol.* 43: 506-520, which is incorporated by reference). The cells from previous isolations have been found to be more than 99% viable, as determined by trypan blue exclusion, and to contain less than 2% non-parenchymal cells.

The PRH cells are then seeded into the well at a density of $2 \times 10^4$ cells/well (1.35 cm$^2$ culture surface area) and incubated in a humidified air, 5% $CO_2$ incubator at 37° C. The culture vessel is replenished with fresh medium after 4-6 hours, and every 72 hours afterwards, or as needed using DMEM medium.

Figure 13:
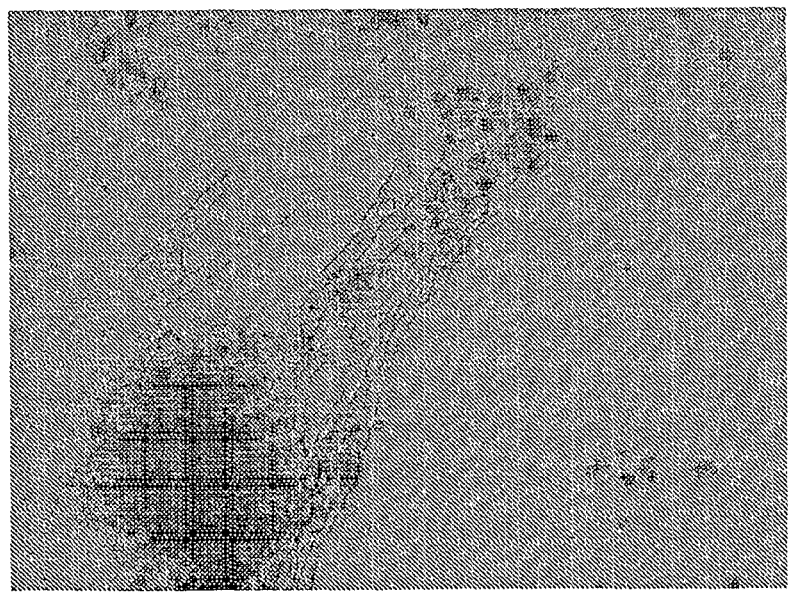
FIG. 13 is an optical micrograph, top view, of Primary Rat Hepatocytes at 10 days post-harvest/post-seed, according to Example 4. Note formation of cellular strands or "cords" typical of primary hepatocytes in vitro. Dark area indicates dense, multi-layer growth.

FIG. 13 is an optical micrograph of PRH at 10 days post-harvest/post-seed.

Example 5

Proliferation of Mouse Embryonic Stem Cells without Fibroblast feeder Layer

Figure 14:
FIG. 14 is an optical micrograph, top view, of Mouse Embryonic Stem Cells (mESC) at 2 days post-seed, according to Example 5. Note formation of small cluster of cells. mESC are grown directly on coated vessel bottom surface, without use of feeder cells.

Mouse Embryonic Stem Cells (mESC) were cultured in the present invention. mESC were prepared according to the following: mESC were commercially obtained from Chemicon International, Temecula, Calif. (PluriStem™ B6-White™ Murine ES, 8-day embryo) and initially seeded on a mouse fibroblast feeder layer grown on TC-grade polystyrene cultureware according to the method of Matise, et al. (Matise, M. P., Auerbach, W., & Joyner, A. L. (1999). Production of targeted ES cell clones. In: A. L. Joyner (Ed.), *Gene targeting: a practical approach, 2nd Edition* (pp. 101-131). Oxford (England): Oxford University Press, which is incorporated by reference). mESC were grown for 2 days and removed by standard trypsinization (0.25% trypsin in Hank's Solution). Detached mESC were isolated and seeded directly (without a feeder layer) onto the bottom surface of a gas-permeable vessel prepared as per Example 1. FIG. 14 is an optical micrograph of mESC at 2 days post-seed on the present invention. mESC shown in FIG. 15 were then successfully passaged (trypsinized, isolated, and re-seeded) 2 additional times (into freshly prepared vessels according to Ex. 1, each passage at 2 days post-seed) prior to a failure to attach to the substrate. No obvious signs of differentiation were observed.

Example 6

Long-Term Culture of Chronic Lymphoid Leukemia Cells while Retaining Pertinent Cell Surface Proteins Chronic Lymphoid Leukemia Cells (CLL), anchorage-independent suspension leukocytes, were cultured in the present invention. Primary CLL cells were isolated and prepared according to the following: Blood was withdrawn from a leukemic patient via venipuncture and isolated according to the following standard procedure:

1. In hood: Add blood to Vacutainer CPT cell preparation tube with sodium citrate
2. Invert (mix) blood samples approx. 20 times (no vortex)
3. Centrifuge at 2800 rpms for 20 mins at RT (spin in large buckets w/paper for balance and no brakes).
4. In hood: Remove appox ½ of plasma (clear/yellow liquid), transfer buffy coat (white, cloudy layer) and remaining plasma into 15 ml tube.
5. BTV w/1×PBS
6. Centrifuge for 15 mins at 1200 rpms
7. Aspirate supernatant, resuspend pellet and BTV 10 ml w/1×PBS, mix well, count.
8. Centrifuge for 10 mins at 1200 rpms, aspirate
9. Resuspend cell pellet in RPMI 1640 at RT
10. Aliquot into vials
    a. No more than 15 vials
    b. If ≧100 million, do 25-30 million/vial
    c. If ≦10 million, do only one vial
    d. If ≧10 million but ≦100 million, do 10 million/vial The CLL cells were then seeded into a well (standard preparation per Example 2) at a density of $1 \times 10^6$ cells/well (1.35 cm$^2$ culture surface area) in DMEM and incubated in a humidified air, 5% $CO_2$ incubator at 37° C. The culture vessel is replenished with fresh media after 5 days and every 5 days afterwards, or as needed using supplemented medium. CLL cells were cultured for 57 days at which time they were counted using a hemocytometer and stained with trypan blue viability stain. The cells were found to be 91% viable. The cells were then analyzed using flow cytometry and were found to be expressing CD5 and CD19 surface antigens which are indicative of active CLL leukocytes.

Figure 15:
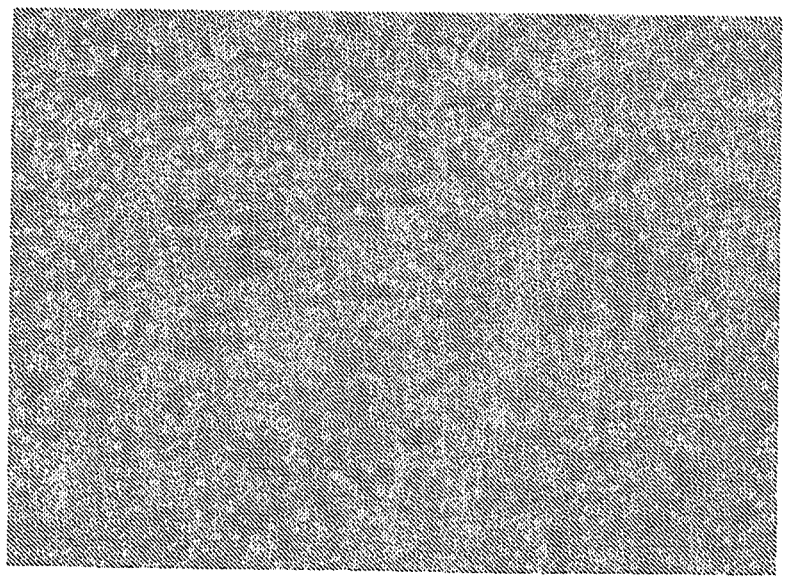
FIG. 15 is an optical micrograph, top view, of human Chronic Lymphoid Leukemia cells (CLL) at 2 days post-seed, according to Example 6.

FIG. 15 is an optical micrograph of primary CLL cells at 52 days post-seed in the present invention.

Example 7

Culture of High-Metabolic Functioning Primary Rat Hepatocytes

Primary Rat Hepatocytes (PRH) were cultured in a gas-permeable wells (1.35 cm$^2$ per well culture surface area, similar to that of a standard 24-well plate) for 3 days and the levels of various metabolic processes were compared against those of cells cultured under similar conditions in conventional polystyrene cultureware. PRH were harvested according to the method of Example 4; PRH were then isolated and purified according to the method of LeCluyse, et al. (LeCluyse, Edward L., et al (2004). Isolation and Culture of Primary Human Hepatocytes. From: Methods in Molecular Biology, vol. 290: *Basic Cell Culture Protocols, 3rd Edition*, C. D. Helgason and C. L. Miller, Editors, Humana Press Inc., Totowa, N.J.: 207-230, which is incorporated by reference).

Gas-permeable wells and control polystyrene 24-well plates were coated with Type 1 rat tail collagen according to the following: 2-3 drops of collagen solution (BD catalog no. 354236) was added to each well and distributed over the well bottom surface using a pipette tip. Once an even distribution is achieved, the wells and control plates were stored overnight in an incubator. The following day, the collagen solution is removed via pipette. Vessels are then filled with media and cells at a seeding densities of $3 \times 10^5$ cells/well (density 1) and $1.5 \times 10^5$ cells/well (density 2, half of density 1) and incubated in a humidified air, 5% $CO_2$ incubator at 37° C. After 3 days, the cells were challenged with test chemicals and the media was removed and analyzed by mass spectrometer for signs of chemical species indicative of cytochrome P450 and conjugating enzyme activity: ECOD (7-ethoxycoumarin O-deethylation), and Sulfonation and Glucuronidation of 3-OH-benzo(a)pyrene.

Figures 16, 17:
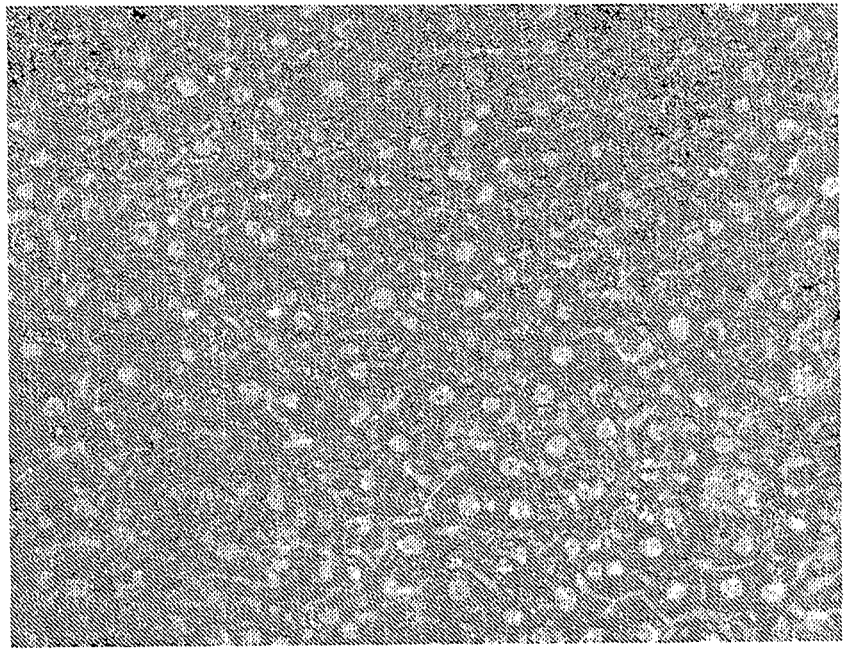
FIG. 16 is an optical micrograph, top view, of Primary Rat Hepatocytes at 3 days post-seed, according to Example 7.
FIG. 17 is a table of results of metabolite data of the Primary Rat Hepatocytes shown in FIG. 16, including ECOD, Sulfonation, and Glucuronidation. Cells cultured in gas-permeable wells showed increases of approximately to 90×, 5×, and 200× in ECOD, Sulfonation, and Glucuronidation activities, respectively, over the gas-impermeable (polystyrene) control wells.

FIG. 16 is an optical micrograph of PRH at 3 days post-seed showing a complete monolayer.

FIG. 17 is a table of results of ECOD, Sulfonation, and Glucuronidation data. As seen, cells cultured in gas-permeable wells showed increases of approximately to 90×, 5×, and 200× in ECOD, Sulfonation, and Glucuronidation processes, respectively, over the controls. The present invention thus promotes strong increases in metabolic detoxification activities by PRH as compared to conventional cultureware.

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements. Thus, while the present invention has been described above with particularity and detail in connection with what is presently deemed to be the most practical and preferred embodiments of the invention, it will be apparent to those of ordinary skill in the art that numerous modifications, including, but not limited to, variations in size, materials, shape, form, function and manner of operation, assembly and use may be made without departing from the principles and concepts set forth herein.

I claim:

1. A process for making cell culture labware, comprising:
   Molding a substantially rigid first material into a rack structure including a plate having substantially planar top and bottom surfaces and at least one hole extending therethrough; and
   subsequently attaching to the rack structure at least one vessel formed of a gas permeable second material and having a bottom portion and a side wall portion extending upwardly from the bottom portion;
   wherein the vessel is directly attached to the bottom surface of the plate beneath the hole, and does not extend through a plane defined by the bottom surface of the plate.

2. The process of claim 1, further comprising molding the vessel against mold surfaces, wherein at least a portion of the mold surfaces is textured.

3. The process of claim 1, wherein attaching the vessel to the rack structure comprises overmolding the vessel onto the rack structure.

4. The process of claim 1, wherein the side wall portion includes an upper surface, and wherein the step of attaching the vessel to the rack structure comprises directly attaching the upper surface to the bottom surface of the plate.

5. The process of claim 4, wherein the plate includes a peripheral skirt element, said skirt element being formed to have one or more windows configured to provide atmospheric ventilation to the vessel exterior.

6. The process of claim 1, wherein the side wall portion includes a top edge that defines an opening having a first perimeter and wherein the hole has a second perimeter.

7. The process of claim 6, wherein the first and second perimeters are substantially the same, such that the opening and the hole are substantially continuous.

8. The process of claim 6, wherein the first perimeter is slightly smaller or larger than the second perimeter.

9. The process of claim 1, further comprising treating at least a portion of the vessel with a plasma.

10. The process of claim 1, further comprising at least partially coating an internal surface of the vessel with a bioactive coating configured to promote attachment and growth of cells.

11. An apparatus, comprising:
    a rack including a plate formed of a substantially rigid first material and having substantially planar top and bottom surfaces and at least one hole extending therethrough;
    at least one vessel formed of a gas-permeable second material and having a bottom portion and a side wall portion extending upwardly from the bottom portion;
    wherein the vessel is directly attached to the bottom surface of the plate beneath the hole, and does not extend through a plane defined by the bottom surface of the plate.

12. The apparatus of claim 11, wherein the vessel is overmolded onto the bottom surface of the plate.

13. The apparatus of claim 11, wherein the sidewall portion includes an upper surface directly attached to the bottom surface of the plate.

14. The apparatus of claim 11, wherein the plate includes a peripheral skirt element, said skirt element having one or more windows configured to provide atmospheric ventilation to the vessel exterior.

15. The apparatus of claim 11, wherein the side wall portion includes a top edge that defines an opening having a first perimeter, and wherein the hole has a second perimeter.

16. The apparatus of claim 15, wherein the first and second perimeters are substantially the same, such that the opening and the hole are substantially continuous.

17. The apparatus of claim 15, wherein the first perimeter is slightly smaller or larger than the second perimeter.

18. The apparatus of claim 11 wherein the substantially rigid first material is a thermoplastic material.

19. The apparatus of claim 11, wherein the gas-permeable second material comprises at least one silicone polymer.

20. The apparatus of claim 11, wherein the gas-permeable second material has an oxygen permeability coefficient greater than or equal to approximately $10 \times 10^{-13}$ [$m^3$ (STP)× cm/($cm^2 \times s \times Pa$)] and a carbon dioxide permeability coefficient of greater than or equal to approximately $25 \times 10^{-13}$ [$m^3$ (STP)×cm/($cm^2 \times s \times Pa$)].

21. The apparatus of claim 11, wherein the gas-permeable second material has an oxygen permeability coefficient greater than or equal to approximately $25 \times 10^{-13}$ [$m^3$ (STP)× cm/($cm^2 \times s \times Pa$)] and a carbon dioxide permeability coefficient of greater than or equal to approximately $50 \times 10^{-13}$ [$m^3$ (STP)×cm/($cm^2 \times s \times Pa$)].

22. The apparatus of claim 11, wherein the side wall portion has an internal surface that is at least partially textured to promote the adhesion and spreading of cells.

23. The apparatus of claim 11, wherein the side wall portion has an internal surface that is at least partially coated with a bioactive coating configured to promote attachment and growth of cells.

* * * * *